(12) United States Patent
Hickling

(10) Patent No.: US 6,862,252 B1
(45) Date of Patent: Mar. 1, 2005

(54) METHOD AND APPARATUS FOR ACOUSTIC DETECTION OF BURIED OBJECTS

(76) Inventor: Robert Hickling, 8306 Huntington Rd., Huntington Woods, MI (US) 48070

( * ) Notice: Subject to any disclaimer, the term of this patent is extended or adjusted under 35 U.S.C. 154(b) by 0 days.

(21) Appl. No.: 10/658,076

(22) Filed: Sep. 9, 2003

Related U.S. Application Data

(63) Continuation-in-part of application No. 10/396,541, filed on Mar. 25, 2003.

(51) Int. Cl.[7] .............................. G01S 3/80; G01N 29/00
(52) U.S. Cl. .......................... 367/88; 367/99; 367/153; 73/594
(58) Field of Search ........................... 367/88, 99, 147, 367/37, 56, 153; 73/594, 602, 649, 661

(56) References Cited

U.S. PATENT DOCUMENTS

| | | | |
|---|---|---|---|
| 5,357,063 A | | 10/1994 | House et al. |
| 5,398,217 A | * | 3/1995 | Cannelli et al. ............. 367/147 |
| 5,563,848 A | * | 10/1996 | Rogers et al. ................ 367/99 |
| 6,055,214 A | * | 4/2000 | Wilk ............................ 367/99 |
| 6,081,481 A | | 6/2000 | Sabatier et al. |
| 6,687,189 B1 | * | 2/2004 | Schaefer et al. ............. 367/147 |
| 6,738,311 B1 | * | 5/2004 | Guigne ......................... 367/88 |

FOREIGN PATENT DOCUMENTS

| | | | | |
|---|---|---|---|---|
| FR | PCT/FR02/00980 | * | 9/2002 | ............ G01V/1/00 |

OTHER PUBLICATIONS

U.S. Appl. No. 10/396,541, Hickling.
J.C. Zwicker &C. W. Kosten, 1949, "Sound Absorbing Materials", Elsevier, New York, NY.
M. A. Biot, 1956, Journ. Acoust. Soc. Amer. 28, 168–191.
N. Xiang & J. M. Sabatier, 2003, Journ. Acoust. Soc. Amer. 113(2), 1333–1341.
D. Donskoy et al, 2002, Journ. Acoust. Soc. Amer. 111(6), 2706–2714.
C. W. Baker, 1973, "Explosions in Air", Univ. of Texas Press, Austin, TX.
M. Loeb & J. L. Fletcher, 1968, Journ. Acoust. Soc. Amer. 44(6), 1524–1528.
W. M. Wright, 1983, Journ. Acoust. Soc. Amer. 73, 1948–1955.

* cited by examiner

*Primary Examiner*—Ian J. Lobo
(74) *Attorney, Agent, or Firm*—Reising, Ethington, Barnes, Kisselle, P.C.

(57) ABSTRACT

Method and apparatus for acoustic detection, location and identification of a buried object using a source emitting bursts of sound that penetrate the ground and return echoes from the object to an array of acoustic vector probes (200) located above the ground. Echoes recorded at the probes in the array, are converted to digital form and fed into a digital signal processor (400) which computes the sound-intensity vector at each probe. Results are displayed on a computer screen or other device (500) permitting an operator to interact with and control the apparatus. The processor controls gating of the bursts of pulsed sound and the duration of the reception of echoes by the array. Additional related features and methods are disclosed.

10 Claims, 2 Drawing Sheets

METHOD AND APPARATUS FOR ACOUSTIC DETECTION OF BURIED OBJECTS

This Application is a Continuation-in-Part of U.S Patent Application Entitled "Acoustic Measurement Method and Apparatus" Ser. No. 10/396,541, Filed 2003, Mar. 25, By, ROBERT HICKLING, The Present Inventor.

TECHNICAL FIELD

The invention relates to the detection, location and identification of buried objects using echoes from bursts of sound penetrating the ground The receiver is an array of recently developed acoustic vector probes (AVPs).

BACKGROUND OF THE INVENTION

Previous Acoustic Methods of Detecting Buried Objects

It has been known for some time that sound can penetrate porous media such as soil and gravel. Early references are
1. C. Zwikker and C. W. Kosten, 1949, "Sound Absorbing Materials", Elsevier, New York
2. M. A. Biot, 1956, "Theory of propagation of elastic waves in a fluid-saturated porous solid, Parts I and II", J. Acoust Soc. Amer. 28, 168–191.

An important application has been the detection of landmines, as described by

3. N. Xiang and J. M. Sabatier, 2003, "An experimental study on antipersonnel landmine detection using acoustic-to-seismic coupling", J. Acoust Soc. Amer., 113(2), 1333–1341.
4. J. M. Sabatier and K E. Gilbert, 2000, "Method for detecting buried objects by measuring seismic vibrations induced by acoustical coupling with a remote source of sound". U.S Pat. No. 6,081,481, Jun. 27, 2000.
5. D. Donskoy, A. Ekimov, N. Sedunov and M. Talonsky, 2002, "Nonlinear seismo-acoustic land mine detection and discrimination", J. Acoust Soc. Amer., 111(6), 2706–2714.

In these methods continuous sound from a loudspeaker penetrate the ground and is reflected by the buried object The presence of the buried object changes the vibrational response of the ground surface and this is used to detect the object. For safety reasons it is necessary to measure the vibrational response of the ground with a non-contact device. Xiang et al, Sabatier et al and Donskoy et al, all use a laser Doppler vibrometer (LDV) to measure the perpendicular component of the vibrational velocity of the solid particles at the surface of the ground. The measurement is made using the Doppler shift in the reflected laser light caused by the vibration of the ground. The LDV scans the surface of the ground at a number of points and the resulting raser distribution is used to determine the presence of a buried object. The loudspeaker operates continuously as the LDV scans the surface.

Another acoustic method for detecting objects buried in the ground has been described by 6. L. J. House and D. B. Pape, 1994, "Method and Apparatus for Acoustic Energy Identification of Objects buried in Soil", U.S Pat. No. 5.357,063, Oct. 18, 1994.

Here the receiver is a standard sound pressure microphone. The LDV approach has been found to be more effective, particularly for mine detection.

However the LDV approach has some serious drawbacks. An LDV system is sophisticated and relatively expensive. Scanning has to be performed with a single LDV because an array of LDVs would be impractical and prohibitively costly. Raster scanning of the surface is very slow. An LDV has to be carefully aligned and requires trained personnel to use it. Maintaining the stability of the LDV system is a major problem. Since the surface of the ground consists of granular material, it is not perfectly flat and the reflected LDV signal is not as strong as it might be. Also the LDV measures only one component of acoustic vibration. In addition, if the loudspeaker and the LDV are mounted on the same vehicle, there will be a vibrational coupling between the two devices causing the LDV to vibrate near the center frequency of the surface vibrations and interfering with the signal received by the LDV. For these reasons the LDV is not an ideal system for use in developing countries where the problem of buried mines is most severe.

Recently Developed Acoustic Vector Probes

Recently a new acoustic instrument, the acoustic vector probe (AVP), has been developed, which can replace the LDV system for detecting buried objects.
The AVP has been described in 7. R. Hickling 2003, "Acoustic Measurement Method and Apparatus", patent application to the United States Patent and Trademark Office, Ser. No. 10/396541, Filing Date Mar. 25, 2003.

The technical information contained in this patent application is hereby incorporated herein by reference. An AVP consists of a tetrahedral arrangement of four small microphones less than 6 mm in size that simultaneously measures at a point in air the three fundamental quantities of acoustics, namely the sound-intensity and sound-velocity vectors, and sound pressure. Sound intensity is the time average of sound power flow per unit area. The time dependence of sound intensity is determined by taking a series of averages over short intervals. AVPs are more accurate, more compact and less expensive than previous instruments for measuring sound intensity. Nested AVPs can be used to make accurate measurements over a broader frequency range than previous instruments. A calibration procedure described by Hickling (Ref.7) ensures the probe is accurate and omnidirectional.

Other Possible Applications of the Invention

In addition to detecting landmines, the AVP apparatus can be used for archeological surveys, crime investigation, detection of insect grubs in the soil and other applications involving detection of buried objects.

BACKGROUND OF THE INVENTION— OBJECTS AND ADVANTAGES

What is needed and desired is:
(a) an acoustic vector probe (AVP) apparatus that is simple, rugged, inexpensive and easily handled, particularly for use in developing countries.
(b) an apparatus where an array of AVPs avoids the need for scanning the surface of the ground.
(c) an apparatus that provides rapid acquisition of data
(d) an apparatus where ensemble averaging can be applied to the entire array of AVPs.
(e) an apparatus that measures all three components of sound power flow to better determine the location and nature of a buried object.
(f) an apparatus that is stable (g) an apparatus that can be controlled interactively by the operator to obtain as much information as possible about a buried object Further objects and advantages of this invention will become apparent from a consideration of the following description and drawings.

SUMMARY OF THE INVENTION

The present invention includes and utilizes an array of my acoustic vector probes and an impulsive sound source, together with instrumentation and method for detecting, locating and identifying buried objects.

Comparison between the LDV and AVP Approaches

The fundamental difference between the LDV and the AVP approaches is that the LDV measures the component of velocity of solid particles perpendicular to the ground, whereas the AVP measures all three components of the sound-intensity vector in the air near the ground. The AVP determines both the magnitude and direction of the reflected sound. Sound reflected back from a buried object travels through the pores of the material in the ground, exciting both the solid particles surrounding the pores and the air within the pores. The LDV measures the response of the solid particles at the surface while the AVP measures the response of the air at the surface, Both types of measurement can be used to detect buried objects. The AVP approach however provides information about the direction of sound propagation, which increases its detection capability. AVPs are small, rugged and inexpensive and can easily be formed into an array. An array of AVPs acquires data more rapidly than scanning with an LDV.

Sources of Pulsed Sound

In the LDV method, sound in various forms is generated continuously with a loudspeaker. Since an LDV uses light there is, in principle, no interference with sound. Hence the LDV can observe the response of the surface of the ground while the loudspeaker is operating. On the other hand with AVPs, continuous incident sound would be superimposed on echoes from the buried object To avoid this, pulsed sound is used to separate incident sound from reflected sound. The source of pulsed-sound is an appropriate distance above the array of AVPs and the sound bursts emanating from it are powerful enough to exceed background noise and provide a strong echo from a buried object. A suitable source could be one of the following: a pyrotechnics system, a gun, an electrical discharge or other similar device. Information on the sound generated by these types of sources is provided in 8. C. W. Baker, 1973, "Explosions in Air", University of Texas Press, Austin Tex.
9. K Loeb and J. L. Fletcher, 1968, "Impulse Duration and Temporary Threshold Shift", J. Acoust. Soc. Amer. 44(6), 15241528.
10. W. M. Wright, 1983, "Propagation in air of N waves produced by sparks", J. Acoust. Soc. Amer. 73, 1948–1955.

Loeb and Fletcher simulate gun shots with electrical discharges. Such short sound bursts are ideal for this invention. A detailed explanation is given later. It is conceivable that signal processing could be used to separate continuous incident sound from continuous reflected sound but this would involve a complex procedure, outside the scope of the present invention.

DETAILED DESCRIPTION OF THE PREFERRED EMBODIMENT

Figure 1:
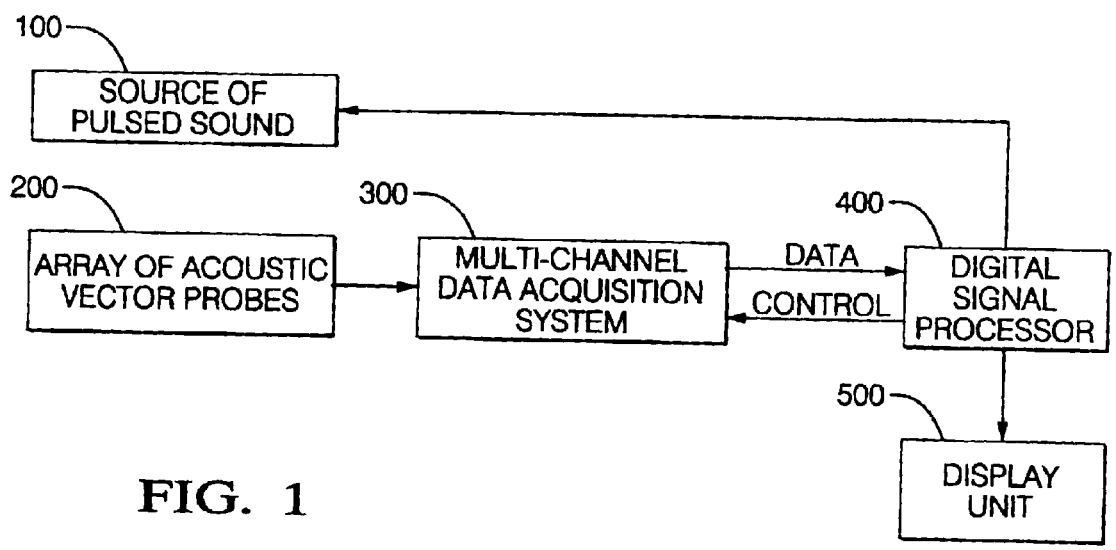
FIG. 1 is a block diagram showing an array of acoustic vector probes, a multi-channel data-acquisition system for rapid analog to digital conversion and temporary data storage, a signal processor, a display unit, and a source of pulsed sound controlled by the signal processor.
Figure 2:
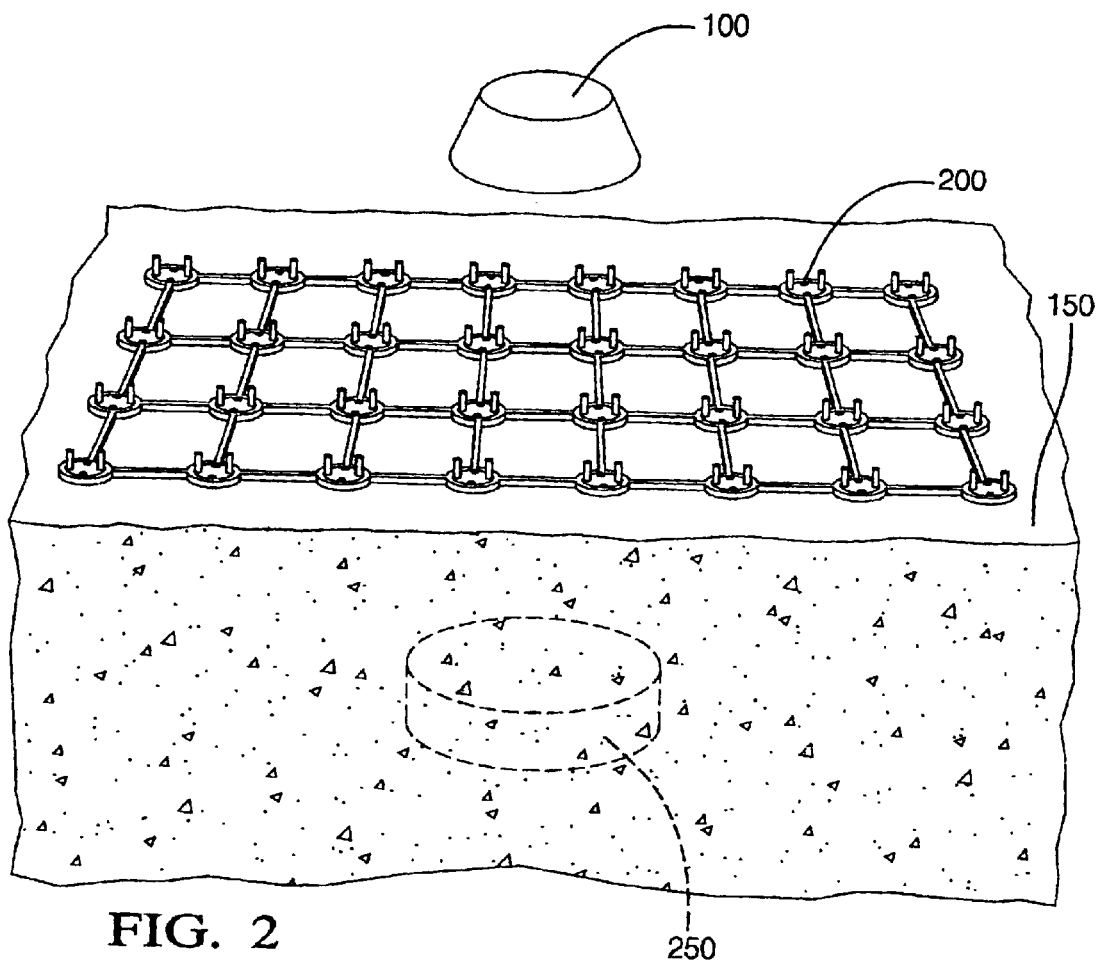
FIG. 2 depicts an array of acoustic vector probes in proximity to the ground together with a source of pulsed sound and a buried object.
Figure 3:
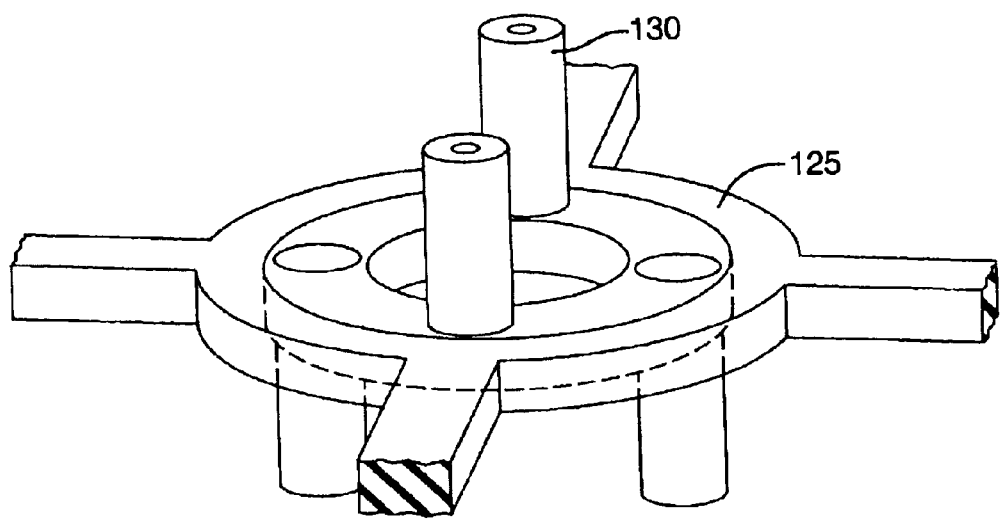
FIG. 3 illustrates a method of constructing the array of acoustic vector probes to include vibration isolation, using a ring or grommet of pliant material.

FIG. 1 is a block diagram illustrating the acoustic detection apparatus of the present invention. Block 200 represents an array of AVPs near the ground while block 100, above the array, is a source of pulsed sound that penetrates the ground. The pulsed sound can be generated by a pyrotechnics device, electric discharge or other equivalent means. Block 300 represents a multi-channel data-acquisition system for rapid analog to digital conversion of the signals from the array, and for data storage, prior to input to the digital signal processor represented by block 400. The processor computes the three components of the sound-intensity vector at each AVP in the array, interpreting the data and displaying the results with an output device 500 such as a monitor screen, which can be hand held or of standard size. The sound-intensity vector is used to detect, locate and identify buried objects. The processor 400 triggers the source of pulsed sound 100, and gates the sound bursts received from the array 200. FIG. 2 depicts an array 200 of any convenient number of AVPs close to the ground 150, together with a source of pulsed sound 100 above the array. In the ground is a buried object 250 differing in its mechanical properties from the porous material surrounding it.. An AVP measures the sound-intensity vector. FIG. 3 illustrates a construction 125 isolating each AVP 130 in the array from interference from vibration induced by random disturbances and by the sound bursts from the acoustic source. The construction can include a ring or grommet of pliant material.

Use of the array involves the rapid intake of a large amount of data Each AVP is sampled simultaneously, with the total number of channels sampled being four times the number of AVPs. This multi-channel intake can be accomplished using available signal processing techniques, the details of which are outside the scope of the present invention.

Figure 4:
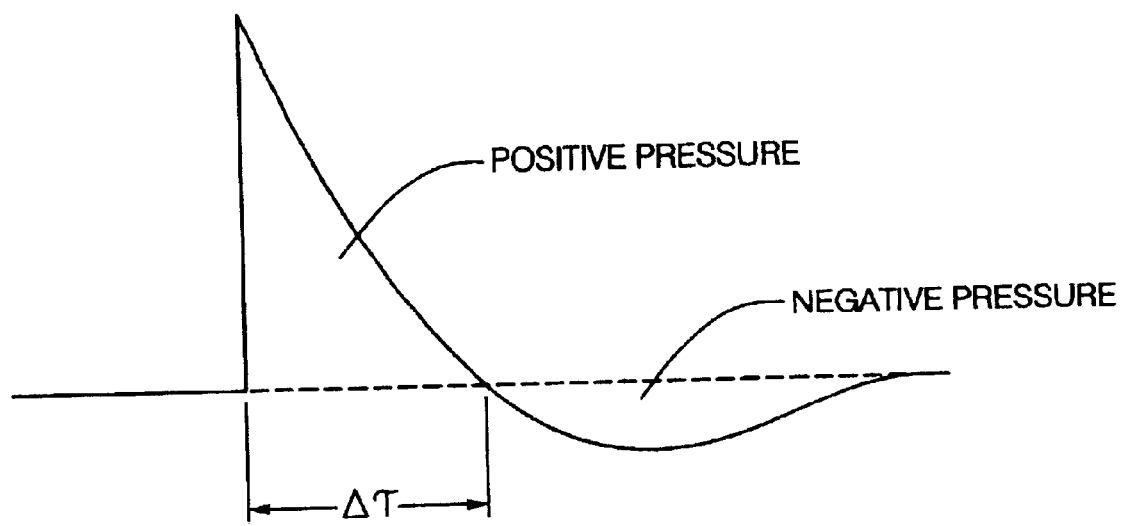
FIG. 4 shows the shape of a sound pulse in air generated by a pyrotechnics system or an electric discharge or other similar source.

FIG. 4 shows a typical pressure-time trace of a pulse from the source of sound pulses. The first part of the pulse, of durations $\Delta\tau$, shows a positive pressure with a steep front and gradual decay, followed in turn by a region of negative pressure. The purpose of the sound pulse is to separate incident from reflected sound sensed by the array of AVPs. Typically the duration of the positive leading section of the sound pulse $\Delta\tau$ in FIG. 4 is about 0.05 to 0.2 ms or longer. A sound pulse of this type contains a wide range of frequencies, particularly frequencies below about 1 kHz which have been found to be best for penetrating the ground. Generally the amplitude of a sound pulse will significantly exceed background noise.

Assuming the source of pulsed sound 100 is about 1 m above the ground and that the speed of sound in air is about 345 m/s, the pulse takes about 3 ms to reach the ground. Signals from the array 200 are gated by the digital signal processor 400 so that neither the pulse nor its first reflection from the ground surface is acquired by the multi-channel data acquisition system 300. The sound pulse penetrates the ground and is reflected back by the buried object which typically might be about 0.05 m from the surface. The round-trip distance in the ground to the object and back to the surface is then about 0.1 m. Typically the speed of sound in the porous material of the ground can be about 250 m/s or less, so that the first part of the echo from the buried object reaches the array of AVPs more than 0.4 ms after the incident pulse reached the ground. At this point the multi-channel data acquisition system 300 has been switched on to receive the return signal. The next sound pulse from the source 100 does not occur until after the return signal has been received completely and analyzed by the processor. Care has to be taken to ensure that the incident pulse and its first reflection are not received at any of the AVPs in the array before the arrival of the return signal from beneath the surface of the ground. This limits the size of the array. For example if the source is about 1 m above the center of the array, the dimension of the array cannot be much greater than about 1 m. In general the source of pulsed sound should be located above the center of the array and the greatest dimension of the ray should be less than or comparable to the distance of the source above the ground. The sound pulse from the source incident on the ground can be strengthened by placing the source thin an acoustic reflector as shown in FIG. 2 where the acoustic reflector houses the pulsed sound source.

The return signal is prolonged in time compared to the incident sound pulse, due to the different conditions and transmission speeds in the porous material and to possible resonances of the buried object The leading edge of the return signal will generally be less steep than that of the incident signal. The return signal represents the impulse response of the porous material of the ground and the buried object (if present) to the incident sound pulse, which is converted to the equivalent frequency responses by the sound-intensity measurement of the AVP. This can be ensemble averaged over a number of sound pulses from the source. The frequency response of the return signal includes both linear and nonlinear effects, as described by Donskoy et al and others. The nature of the frequency response can be changed by changing the characteristics of the sound pulse from the source. Also the frequency response can be filtered to investigate any frequency bands of interest.

The return signal can be gated to exclude reflections from solid layers that may lie beneath the buried object. Gating both of the sound source and of the latter part of the echo can be controlled by the operator of the apparatus. The operator can also control frequency filtering of the return signal. After computing the sound-intensity vector at each AVP, the data are analyzed by the processor to detect, locate and identify the buried object. Timing of the interval between sound pulses is adjusted to allow the return signal to reach all the AVPs in the array and to give the processor time to perform its computations. The results are displayed either on a monitor screen, which can be hand held or of standard size, or with some other type of output device. The operator of the apparatus can, if desired, adjust the position of the array to obtain more information about a buried object While the invention has been described by reference to certain preferred embodiments, it should be understood that numerous changes could be made within the spirit and scope of the inventive concepts described. Accordingly it is intended that the invention not be limited to the disclosed embodiments, but that it have the full scope permitted by the language of the following claims.

What is claimed is:

1. Acoustic apparatus for detecting, locating and identifying buried objects comprising:

an array of acoustic vector probes near the surface of the ground, each of said probes comprises four microphones spatially positioned to define vertices of a regular tetrahedron;

a source of intense sound pulses of short duration for penetrating the porous structure of the ground;

said probes in said array connected to a multi-channel data acquisition system for rapid conversion of analog signals to digital form and for temporary data storage;

said multi-channel system providing input to a digital signal processor programmed to compute the sound-intensity vector at each probe in said array;

said processor connected to a device for outputting the results of the computations; and said processor controlling both said source of pulsed sound and said multi-channel data acquisition system.

2. The invention as in claim 1 wherein each acoustic vector probe in said array is isolated to prevent vibrational interference from random disturbances and from said source of pulsed sound.

3. The invention as in claim 1 wherein said source of pulsed sound is a pyrotechnics system or a generator of electrical sparks.

4. The invention as in claim 1 wherein the pulses from said source of pulsed sound are strengthened by means of an acoustic reflector.

5. The invention as in claim 1 wherein the sound pulses from said source do not overlap the echoes from a buried object.

6. The invention as in claim 1 wherein the said source of sound pulses is approximately centered above said array of acoustic vector probes.

7. The invention as in claim 1 wherein the greatest dimension of said array of acoustic vector probes is approximately the distance of said source of sound pulses from the array.

8. The invention as in claim 1 wherein said processor controls the duration of the reception of echoes by said array.

9. The invention as in claim 1 wherein said output device enables an operator to use said acoustic apparatus interactively to detect, located and identify buried objects, by adjusting the timing and duration of said sound pulses, by ensemble averaging said sound-intensity data, by filtering said data into any desired frequency bands and by adjusting the position of said array of acoustic vector probes and of said source of pulsed sound.

10. The invention as in claim 1 wherein each probe in said array includes said four microphones supported at the vertices of said regular tetrahedron on posts extending in pairs in opposite directions from a ring, the posts being parallel to the axis of the ring, which is perpendicular to the array.

* * * * *

UNITED STATES PATENT AND TRADEMARK OFFICE
CERTIFICATE OF CORRECTION

PATENT NO. : 6,862,252 B1
DATED : March 1, 2005
INVENTOR(S) : Robert Hickling

It is certified that error appears in the above-identified patent and that said Letters Patent is hereby corrected as shown below:

Column 1,
Line 44, replace "penetrate" with -- penetrates --
Line 56, replace "raser" with -- raster --

Column 4,
Line 57, replace "durations" with -- duration --

Column 5,
Line 30, replace "thin" with -- within --
Line 42, replace "responses" with -- response --

Column 6,
Line 53, replace "located" with -- locate --

Signed and Sealed this

Seventeenth Day of May, 2005

JON W. DUDAS
*Director of the United States Patent and Trademark Office*